(12) United States Patent
Kassab

(10) Patent No.: US 11,234,722 B2
(45) Date of Patent: Feb. 1, 2022

(54) DEVICES, SYSTEMS, AND METHODS TO GENERATE A BYPASS LUMEN IN CONNECTION WITH A CHRONIC TOTAL OCCLUSION PROCEDURE

(71) Applicant: Ghassan S. Kassab, La Jolla, CA (US)

(72) Inventor: Ghassan S. Kassab, La Jolla, CA (US)

( * ) Notice: Subject to any disclaimer, the term of this patent is extended or adjusted under 35 U.S.C. 154(b) by 221 days.

(21) Appl. No.: 15/669,651

(22) Filed: Aug. 4, 2017

(65) Prior Publication Data
US 2018/0036021 A1 Feb. 8, 2018

Related U.S. Application Data

(60) Provisional application No. 62/370,753, filed on Aug. 4, 2016.

(51) Int. Cl.
| | | |
|---|---|---|
| A61B 17/22 | (2006.01) | |
| A61B 17/34 | (2006.01) | |
| A61B 17/00 | (2006.01) | |
| A61B 17/32 | (2006.01) | |

(52) U.S. Cl.
CPC .......... *A61B 17/22* (2013.01); *A61B 17/3417* (2013.01); *A61B 17/3478* (2013.01); *A61B 2017/00026* (2013.01); *A61B 2017/00252* (2013.01); *A61B 2017/00876* (2013.01); *A61B 2017/22061* (2013.01); *A61B 2017/22095* (2013.01); *A61B 2017/320048* (2013.01)

(58) Field of Classification Search
CPC .......... A61B 2017/22095; A61B 2017/22094; A61B 2017/00026; A61B 2017/00252; A61M 25/0194; A61M 2025/0197
See application file for complete search history.

(56) References Cited

U.S. PATENT DOCUMENTS

| | | | |
|---|---|---|---|
| 7,454,244 B2 | 11/2008 | Kassab et al. | |
| 9,462,960 B2 | 10/2016 | Kassab | |
| 2007/0093780 A1* | 4/2007 | Kugler | A61B 17/221 604/510 |
| 2008/0004647 A1* | 1/2008 | To | A61B 17/22 606/159 |
| 2013/0150880 A1* | 6/2013 | Anderson | A61B 17/3207 606/194 |
| 2015/0196360 A1* | 7/2015 | Grantham | A61B 18/245 600/427 |
| 2015/0351782 A1* | 12/2015 | Kangas | A61B 17/3207 604/22 |
| 2016/0008584 A1* | 1/2016 | Root | A61M 25/09 604/510 |

* cited by examiner

*Primary Examiner* — Majid Jamialahmadi
(74) *Attorney, Agent, or Firm* — 3DT Holdings, LLC

(57) ABSTRACT

Devices, systems, and methods to generate a bypass lumen in connection with a chronic total occlusion procedure. An exemplary method comprises introducing at least part of a first elongated body into a lumen of an artery so that a distal tip of the first elongated body is positioned on a first side of an occlusion within the lumen of the artery; inserting the distal tip of the first elongated body into a wall of the artery in between a tunica media and a tunica intima of the artery; advancing the distal tip of the first elongated body in between the tunica media and the tunica intima; and further advancing the distal tip of the first elongated body back into the lumen of the artery to generate a bypass lumen and so that the distal tip is positioned on an opposite second side of the occlusion within the lumen.

10 Claims, 4 Drawing Sheets

DEVICES, SYSTEMS, AND METHODS TO GENERATE A BYPASS LUMEN IN CONNECTION WITH A CHRONIC TOTAL OCCLUSION PROCEDURE

PRIORITY

The present application is related to, and claims the priority benefit of, U.S. Provisional Patent Application Ser. No. 62/370,753, filed Aug. 4, 2017, the contents of which are hereby incorporated into the present disclosure directly and by reference in their entirety.

INCORPORATION BY REFERENCE

U.S. patent application Ser. No. 14/215,012 of Kassab, filed Mar. 16, 2014 and issued as U.S. Pat. No. 9,462,960 on Oct. 11, 2016, is hereby incorporated by reference herein in its entirety.

BACKGROUND

Chronic Total Occlusions (CTOs) exist when a vessel, such as an artery, is completely blocked, due to calcification, thrombus, or other blockage. Traditional balloon angioplasty procedures can therefore not be performed because, for example, a wire cannot successfully pierce the blockage to permit a balloon catheter to operate therethrough During CTO treatment procedures, the treating physicians/interventionalists frequently need to enter the sub-intimal space using some sort of device as the lumens of the vessels at issue are completely blocked. The general problem is that the physicians do not know whether the devices they are using are in the lumen of the vessel or in the sub-intimal space of the vessel.

Current CTO treatment can involve the use of two devices, namely a first device antegrade to the CTO and a second device retrograde to the CTO, whereby the two devices are effectively connected to one another by ballooning the intima. Such a procedure also requires both devices to either have their distal ends within the lumen at the same time or in the subintimal space at the same time for the procedure to work. Furthermore, the physician would need to know whether the tips of the two devices physically touch one another. Said treatment procedure is not only difficult to perform, but includes several guesses as to where the distal portions of the two devices are relative to one another, calling into question the effectiveness and potential safety of such a procedure.

In view of the same, methods to treat CTOs and devices and systems useful to perform the same would be well appreciated in the marketplace.

BRIEF SUMMARY

The present disclosure includes disclosure of a method, comprising the steps of introducing at least part of a first elongated body into a lumen of an artery so that a distal tip of the first elongated body is positioned on a first side of an occlusion within the lumen of the artery; inserting the distal tip of the first elongated body into a wall of the artery in between a tunica media and a tunica intima of the artery; advancing the distal tip of the first elongated body in between the tunica media and the tunica intima; and further advancing the distal tip of the first elongated body back into the lumen of the artery to generate a bypass lumen and so that the distal tip is positioned on an opposite second side of the occlusion within the lumen of the artery. The present disclosure includes disclosure of a method, further comprising the steps of advancing a balloon catheter over at least part of the first elongated body so that a balloon of the balloon catheter is positioned within the bypass lumen between the tunica media and the tunica intima of the artery adjacent to the occlusion; and inflating the balloon within the bypass lumen so to expand the bypass lumen. The present disclosure includes disclosure of a method, further comprising the steps of deflating the balloon; and removing the balloon catheter and the at least part of the first elongated body from the artery to allow blood present within the lumen of the artery to flow through the bypass lumen.

The present disclosure includes disclosure of a method, further comprising the step of introducing at least part of a second elongated body into the lumen of the artery so that a distal tip of the second elongated body is positioned on the opposite second side of the occlusion within the lumen of the artery; wherein the step of further advancing is performed to further advance the distal tip of the first elongated body so that it contacts the distal tip of the second elongated body. The present disclosure includes disclosure of a method, wherein the distal tip of the first elongated body is magnetically attracted to the distal tip of the second elongated body. The present disclosure includes disclosure of a method, wherein the first elongated body comprises an impedance detector, the impedance detector configured to obtain first impedance data within the lumen and second impedance data within the wall of the artery, wherein the first impedance data is different from the second impedance data. The present disclosure includes disclosure of a method, performed to and sufficient to treat a chronic total occlusion (CTO) condition.

The present disclosure includes disclosure of a method, comprising the steps of introducing at least part of a first elongated body into a lumen of an artery so that a distal tip of the first elongated body is positioned on a first side of an occlusion within the lumen of the artery; inserting the distal tip of the first elongated body into a wall of the artery in between a tunica media and a tunica intima of the artery; advancing the distal tip of the first elongated body in between the tunica media and the tunica intima; further advancing the distal tip of the first elongated body back into the lumen of the artery to generate a bypass lumen and so that the distal tip is positioned on an opposite second side of the occlusion within the lumen of the artery; advancing a balloon catheter over at least part of the first elongated body so that a balloon of the balloon catheter is positioned within the bypass lumen between the tunica media and the tunica intima of the artery adjacent to the occlusion; inflating the balloon within the bypass lumen so to expand the bypass lumen; deflating the balloon; and removing the balloon catheter from the artery to allow blood present within the lumen of the artery to flow through the bypass lumen.

The present disclosure includes disclosure of a method, further comprising the step of introducing at least part of a second elongated body into the lumen of the artery so that a distal tip of the second elongated body is positioned on the opposite second side of the occlusion within the lumen of the artery; wherein the step of further advancing is performed to further advance the distal tip of the first elongated body so that it contacts the distal tip of the second elongated body. The present disclosure includes disclosure of a method, wherein the distal tip of the first elongated body is magnetically attracted to the distal tip of the second elongated body. The present disclosure includes disclosure of a method, wherein the first elongated body comprises an impedance detector, the impedance detector configured to obtain first impedance data within the lumen and second impedance data within the wall of the artery, wherein the first impedance data is different from the second impedance data. The present disclosure includes disclosure of a method, performed to and sufficient to treat a chronic total occlusion (CTO) condition.

The present disclosure includes disclosure of a device, comprising a first elongated body and a first element positioned at or near the distal end of the first elongated body; wherein the device is configured to be introduced, at least partially, into a lumen of an artery so that a distal tip of the first elongated body is positioned on a first side of an occlusion within the lumen of the artery, whereby the distal tip can be inserted into a wall of the artery in between a tunica media and a tunica intima of the artery, whereby the distal tip can be advanced in between the tunica media and the tunica intima, and whereby the distal tip can be further advanced back into the lumen of the artery to generate a bypass lumen and so that the distal tip is positioned on an opposite second side of the occlusion within the lumen of the artery. The present disclosure includes disclosure of a device, wherein the first element comprises an impedance detector. The present disclosure includes disclosure of a device, wherein the impedance detector is configured to obtain first impedance data within the lumen and second impedance data within the wall of the artery, wherein the first impedance data is different from the second impedance data. The present disclosure includes disclosure of a device, wherein the first element comprises a magnetic element.

The present disclosure includes disclosure of a device, forming part of a system, the system further comprising a second elongated body; and a second element positioned at or near the distal end of the second elongated body. The present disclosure includes disclosure of a device, wherein the first element is magnetically attracted to the second element. The present disclosure includes disclosure of a device, wherein the system further comprises a balloon catheter configured for advancement over at least part of the first elongated body. The present disclosure includes disclosure of a device, wherein a balloon of the balloon catheter is configured for inflation within the bypass lumen so to expand the bypass lumen.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

DETAILED DESCRIPTION

Figure 1:
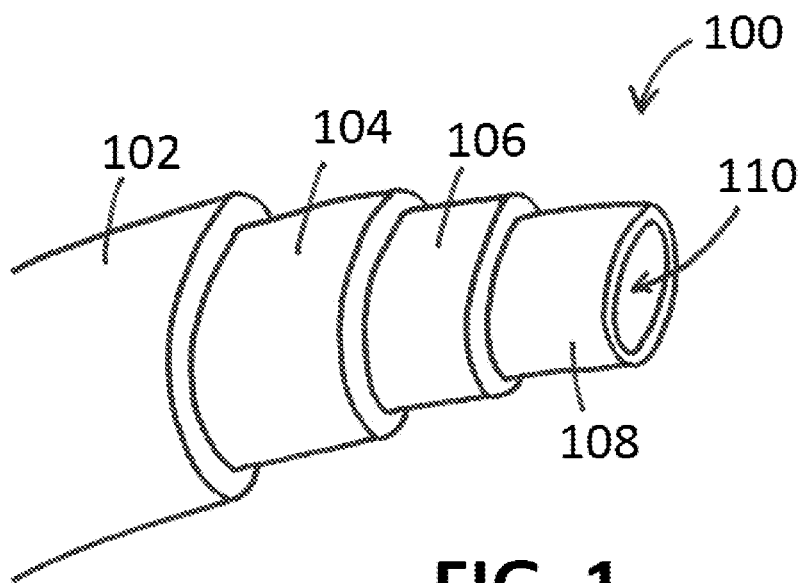
FIG. 1 shows layers of an artery, as referenced herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of methods, and devices and systems useful to perform the same, that allow a treating physician or other interventionalist to sense/identify a general location of a portion of the device or system within the patient, such as within an arterial lumen or within the sub-intimal space.

In at least one embodiment, devices of the present disclosure can be used to obtain impedance data within an electric field, whereby said impedance data, or relative changes thereof, can provide the user of said device with information relating to the specific location of a distal portion of said devices within a vessel lumen, within a sub-intimal space, and/or when one device is in physical contact with another device.

In at least another embodiment, two magnetic portions of said devices can be used to measure a force and hence determine the distance between the two well-defined portions, such as cylinders or other known lengths, such as the known length of the tip of the device.

As referenced above, CTOs relate to situations where a vessel, such as an artery, is completely blocked, due to calcification, thrombus, or other blockage. Traditional balloon angioplasty procedures can therefore not be performed because, for example, a wire cannot successfully pierce the blockage to permit a balloon catheter to operate therethrough.

One known technique to overcome this problem is a subintimal technique, whereby a distal end of a wire advanced into a vessel lumen, pushed sub-intimally (below the intima), advanced past the location of the blockage within the vessel, and then pushed back into the lumen on the other side of the blockage. A balloon catheter can then be advanced over the wire, and the balloon can be inflated/expanded within the sub-intimal space, at the location of the blockage, to effectively create a new lumen that connects the lumen of the vessel distal and proximal to the blockage.

FIG. 1 shows a cut-away portion of an artery 100 (an exemplary vessel of the present disclosure) so that the various tissue layers can be readily identified. Starting from the outside working in, the outermost layer comprises the tunica adventitia 102 (also referred to herein as the adventitia, the tunica externa, or the externa), the next innermost layer comprises the tunica media 104 (also referred to herein as the media), the next innermost layer comprises the tunica intima 106 (also referred to herein as the intima), which itself surrounds a base membrane 108 that surrounds the overall vessel lumen 110. The intima is generally between 0.5 mm and 1.0 mm thick for most arteries.

Figure 2:
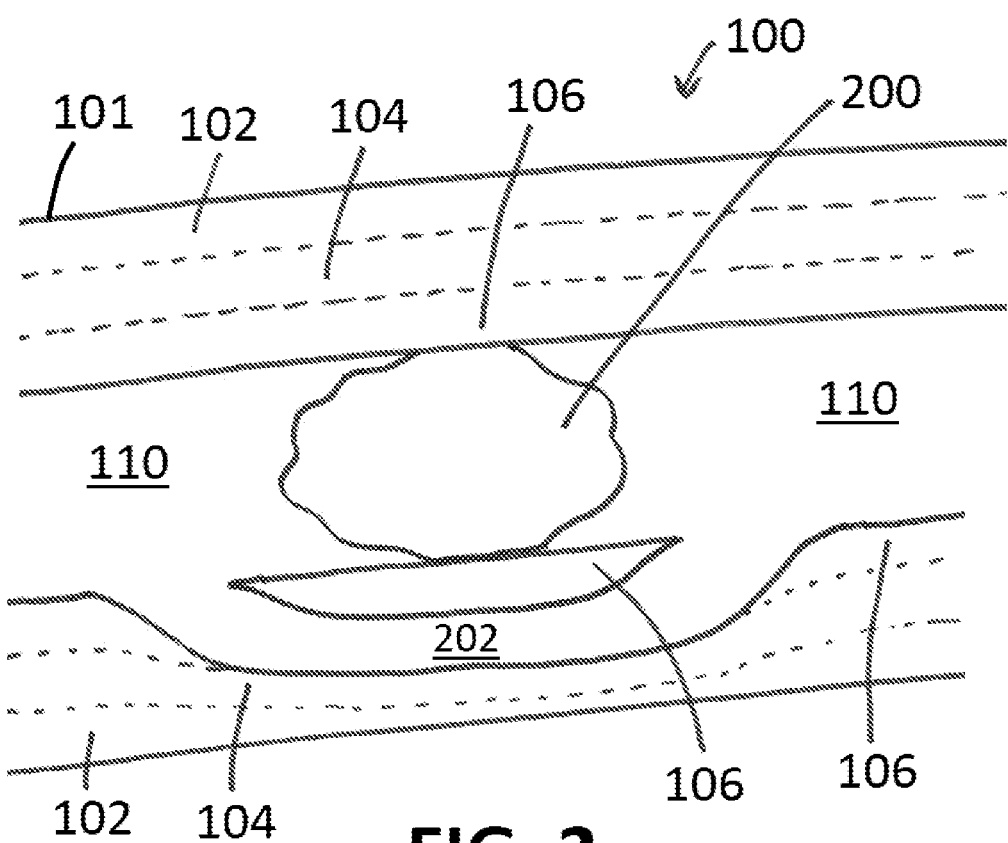
FIG. 2 shows a sectional view of vessel having an effective bypass lumen defined therein relative to an occlusion, according to at least one exemplary embodiment of the present disclosure.

In practice, a guidewire is advanced into the arterial wall itself and into the subintimal space, such as between the intima 106 and the media 104, to generate the effective new lumen, bypassing the occlusion, as referenced above when performing such a CTO bypass procedure. Blood flow can then be restored from the original lumen, through the false/bypass lumen created using the procedure, and back into the original lumen on the other side of the occlusion, such as shown in FIG. 2. As shown therein, a portion of an arterial wall is effectively opened, adjacent to an occlusion 200, so to form a bypass lumen 202, effectively reconnecting the original lumen 110 on both sides of occlusion 200.

Such a procedure has been proven successful to treat CTOs in certain patients, but as noted above, the procedure itself has several pitfalls that are now addressed by way of the present disclosure. In particular, the treating physician or interventionalist generally does not know with any degree of certainty where, for example, the tip of the guidewire is located relative to the occlusion, and therefore generally are required to break certain rules of interventional practice in order to treat CTOs. Such a process introduces significant risk, such as risk of arterial rupture, improper balloon inflation location, and the like.

Figure 3A:
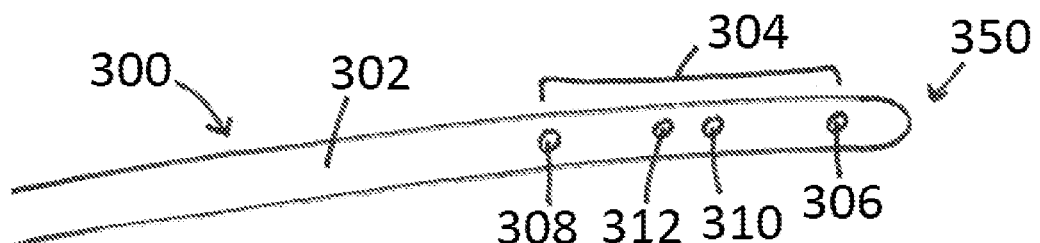
FIG. 3A shows a device configured as an impedance device, according to at least one exemplary embodiment of the present disclosure.

The present disclosure includes disclosure of use of an impedance device, such as a unipolar wire, within the procedure to treat CTOs. Such an exemplary device is shown in FIG. 3A. Other exemplary devices may be as shown or described within any of FIGS. 1A-1F and/or FIGS. 13A-13C of U.S. patent application Ser. No. 14/215,012 of Kassab, filed Mar. 16, 2014 and issued as U.S. Pat. No. 9,462,960 on Oct. 11, 2016, which is incorporated by reference in its entirety herein, so long as said devices are configured and operable as referenced herein.

Impedance device 300, as shown in FIG. 3A, comprises an elongated body 302 configured as wire or a catheter, and comprises an impedance detector 304 thereon, whereby impedance detector comprises one or more excitation electrodes 306, 308 and one or more detection electrodes 310, 312. In at least some embodiments of devices 300 of the present disclosure, devices 300 comprises two detection electrodes 310, 312 positioned in between two excitation electrodes 306, 308, as shown in FIG. 3A. Detector 304 would be positioned at or near a distal tip 350 of device 300, in various embodiments. In at least one embodiment of a unipolar device 300 of the present disclosure, the device 300 comprises one of electrodes 306, 308, 310, 312, and configured to obtain various conductance measurements using impedance within the vessel 100.

Figure 3B:
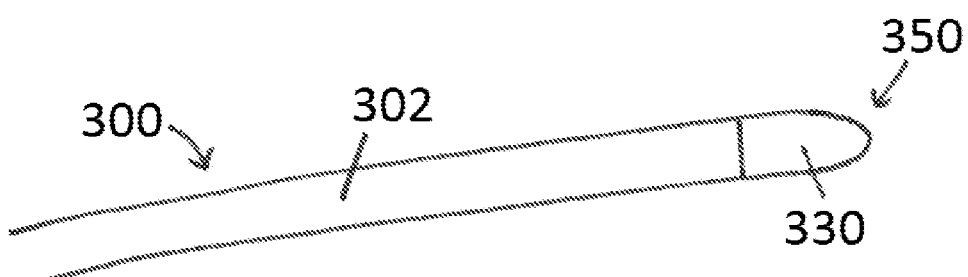
FIG. 3B shows a device having magnetic elements thereon, according to at least one exemplary embodiment of the present disclosure.

An additional approach of the present disclosure is to use a wire (an exemplary device 300) having a tip that is magnetic or ferromagnetic, for example. Such a device 300 could be used with a medical GPS or other detection system, for example, to track the magnetic or ferromagnetic tip of the device 300 within the bloodstream, and to, for example, detect a magnetic or ferromagnetic force between the tips of two devices 300 being advanced toward one another. FIG. 3B shows such an exemplary device 300, having a magnetic element 330 at a distal tip 350 of said device 300. Devices 300 of the present disclosure can have an impedance detector 304 and/or a magnetic element 330, depending on desired configuration. Magnetic elements 330 may be configured as cylinders in various embodiments. Devices 300 can comprise a detector 304 and a magnetic element 330, as may be desired.

In at least one embodiment, two devices 300 are used, each having an electromagnetic tip (an exemplary magnetic element 330 at distal tip 350). A low level electrical charge can be passed through the magnetic material at the tip of the device to make it electromagnetic. Once the two devices 300 approach one another with the electric current turned on, the two tips of the two devices 300 would magnetically connect to one another, and turning off the electric current would allow the two devices 300 to disconnect from one another.

Figure 4:
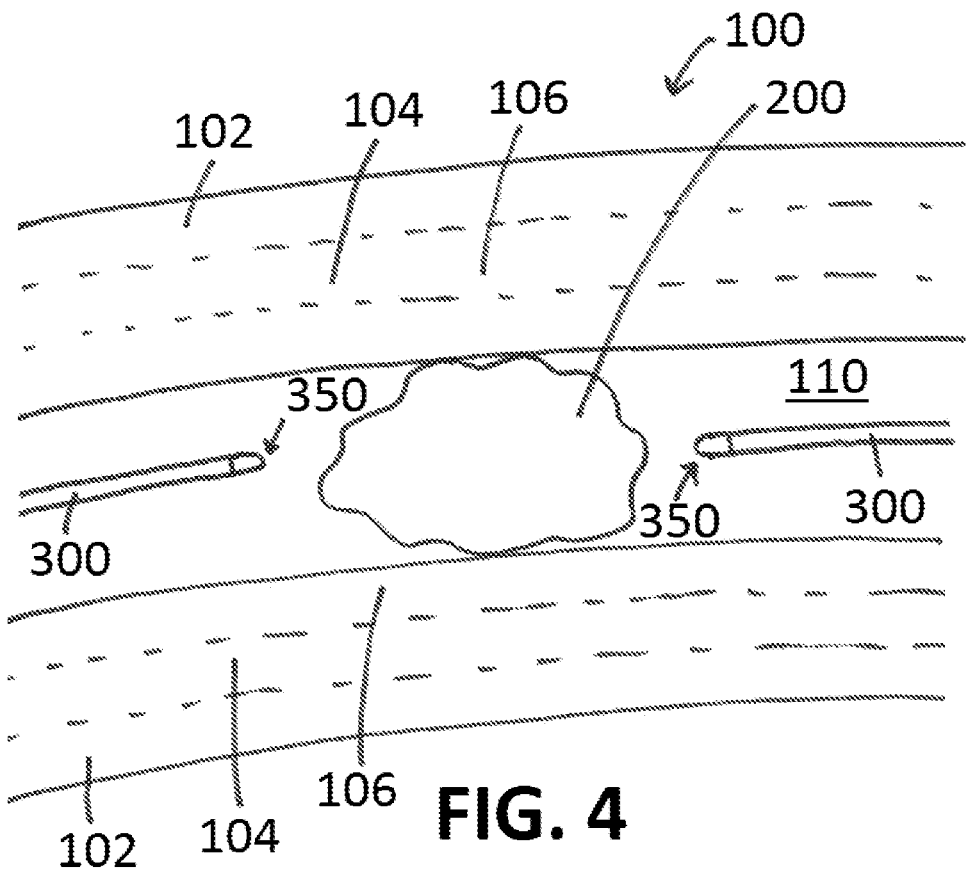
FIG. 4 shows a cut-away view of a vessel having an occlusion therein and distal ends of devices on either relative side of the occlusion, according to at least one exemplary embodiment of the present disclosure.

FIG. 4 shows a cross-section of a vessel 100, similar to as shown in FIG. 2, but whereby the bypass lumen 202 has not yet been formed. Vessel 100, such as an artery, comprises a vessel wall 101. Procedurally, a first wire (first device 300) is advanced through a vessel on a first side of the occlusion 200, either in an antegrade or a retrograde direction. A second device 300 is advanced through vessel 100 on the other side of the occlusion 200, in the other of an antegrade or retrograde direction. FIG. 4 shows distal ends 350 of each device 300 positioned on opposite sides of occlusion 200. Said devices 300 could be advanced through lumen 110 of vessel until they contact occlusion 200, for example, and withdrawn somewhat (if desired) so to continue with the procedure referenced herein. If the devices 300 have magnetic elements 330, the closer they get to one another, the larger the magnetic attraction force becomes with respect to the two devices.

Figure 5:
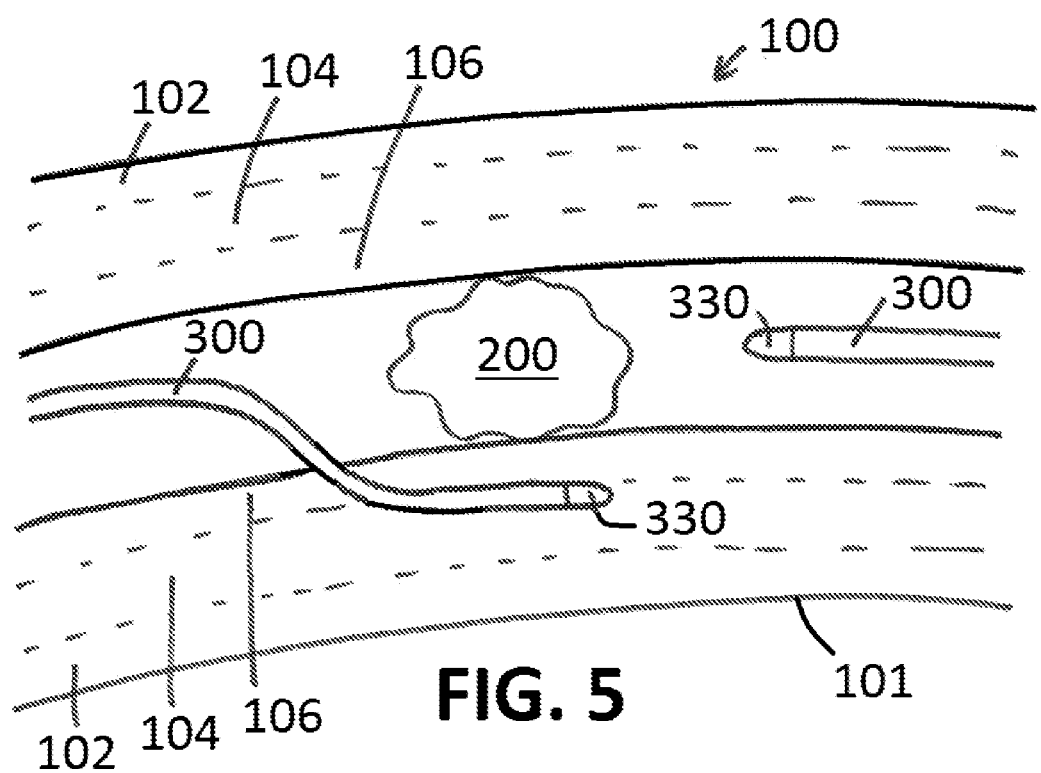
FIG. 5 shows a cut-away view of a vessel having an occlusion therein and a distal end of one device advanced into the tunica intima and advanced between the tunica intima and the tunica media, according to at least one exemplary embodiment of the present disclosure.

FIG. 5 shows the first wire (device 300) entering the vessel at the tunica intima 106 and advanced to a location between the tunica intima 106 and the tunica media 104 (or somewhere within the subintimal space), where it is advanced between the tunica intima 106 and the tunica media 104 (or elsewhere within the subintimal space) until the distal tip 350 of the device 300 is at or relatively past the occlusion 200. Device 300 can be further advanced back through the tunica intima 106 so that the distal tip 350 of the device 300 being advanced between the tunica intima 106 and the tunica media 104 is now present within the lumen 100 again so to approach, and even contact, the distal tip 350 of the other device 300 within the lumen.

By way of identifying relative locations of magnetic elements 330 of the two devices 300, such a procedure can be performed so to generate a bypass lumen 202 that can be subsequently enlarged via balloon expansion, as referenced in further detail herein. Use of a detection system 375, shown in block format in FIG. 6, positioned relative to and/or coupled to one or more of devices 300, can be used to identify relative locations of magnetic elements 330 of the two devices 300, such as visually, magnetically, or electromagnetically. For example, magnetic elements 330 (or other elements detectable using detection system 375) can be visually detected through the patient, or in the case of using magnetic elements 330 that are not electromagnetic, said magnetic elements 330 would be magnetically attracted to one another. Use of electromagnetic elements (exemplary magnetic elements 330) would increase said attraction, and measurements of the attraction of the two electromagnetic elements 330, or one magnetic element 330 or other metallic element and one electromagnetic element 330, identified using detection system 375, would identify an increased attraction as the two magnetic elements 330 approach and even contact one another. Distances between the two magnetic elements 330 can be known in view of the foregoing and in part based upon a known length of the two magnetic elements 330 and/or the known lengths of the devices 300 themselves.

Figure 6:
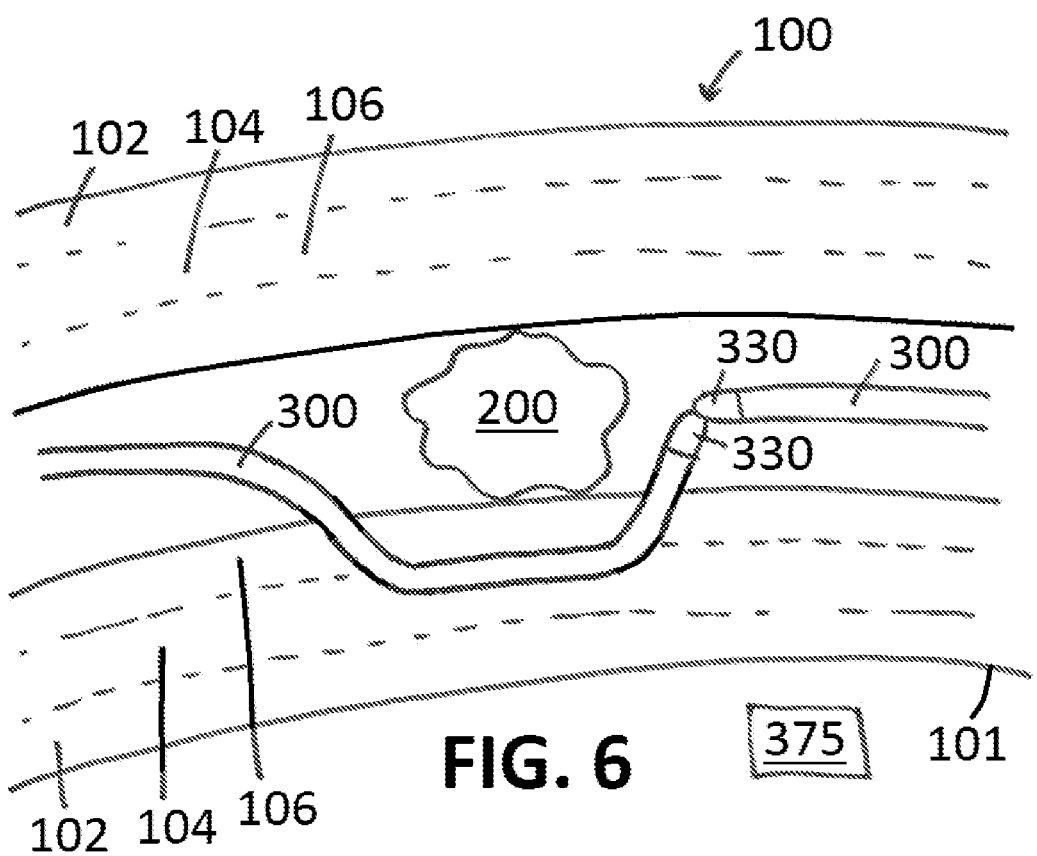
FIG. 6 shows a cut-away view of a vessel having an occlusion therein and a distal end of one device advanced into the tunica intima, advanced between the tunica intima and the tunica media, and advanced back through the tunica intima on the other side of the occlusion so that the distal end contacts a distal end of a second device, according to at least one exemplary embodiment of the present disclosure.

Use of devices 300 having an impedance detector 304 thereon would follow a similar procedure as described in FIGS. 4-6 and above, but instead of magnetic attraction, the impedance detectors 304 would identify changes in impedance indicative of, related to, or between any number of the following: presence of blood, contacting the occlusion 200, contacting vessel 100, contacting the tunica intima 106, contacting the tunica media 104, re-entry into lumen 110, and contacting another device 300. Those changes in impedance/conductance would provide the information to an interventionalist performing the procedure relating to where the impedance detector(s) 304 are during the process. System 375 (such as a console) coupled to one or more of devices 300 would provide the impedance/conductance data to the interventionalist. So to provide certainty with respect to the procedure, for example, the interventionalist would obtain various conductance measurements using impedance detector 304 of device 300 within the lumen 110 of the artery (vessel 100), which would be relatively steady measurements as being indicative of blood. Should the impedance detector 304 contact a wall of the vessel 100 or the occlusion 200 itself, the conductance measurements would change, providing such an indication. The conductance measurements would also change as the detector 304 contacts, is inserted into, is advanced through, and exits out of, a wall of vessel 100 itself. When detector 304 contacts a second device 300, the conductance measurements would change once again. These changes in conductance during the procedure provide the interventionalist with the information necessary to ensure that the procedure is being properly performed to treat the CTO and to effectively create the bypass lumen 202.

Figure 7:
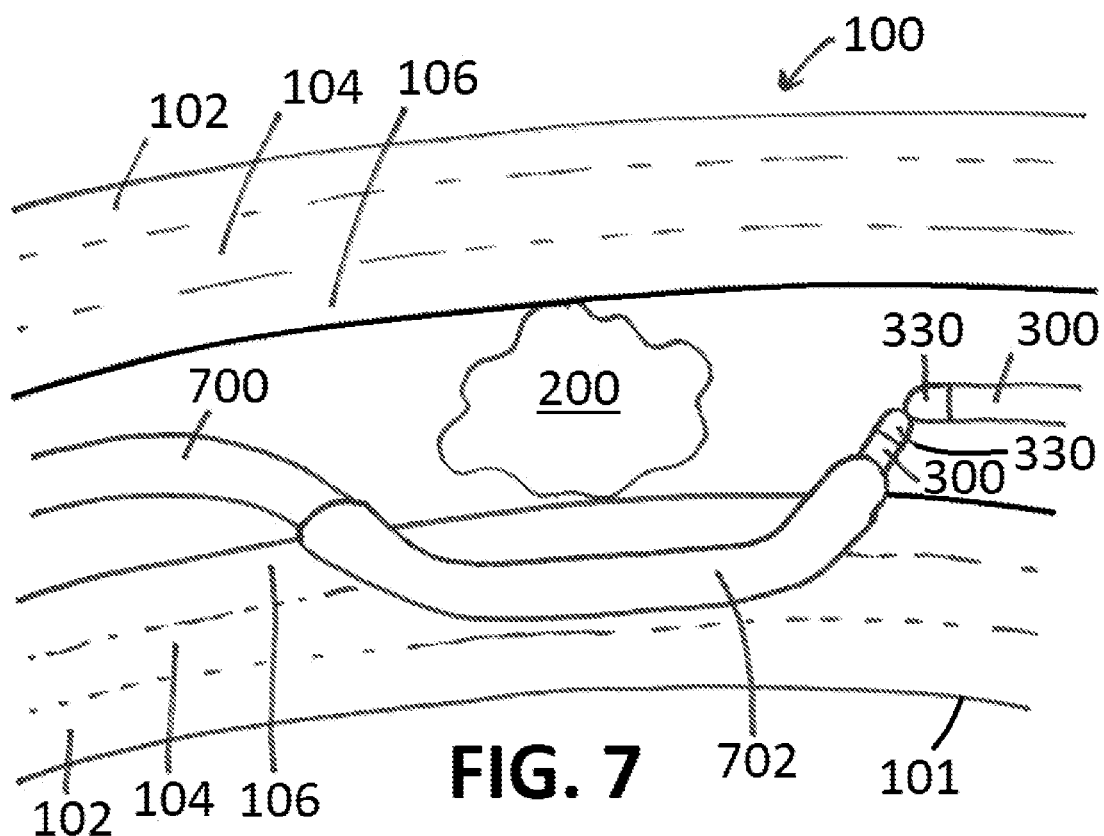
FIG. 7 shows a cut-away view of a vessel having an occlusion therein and a balloon catheter advanced over one of the devices therein, according to at least one exemplary embodiment of the present disclosure.
Figure 8:
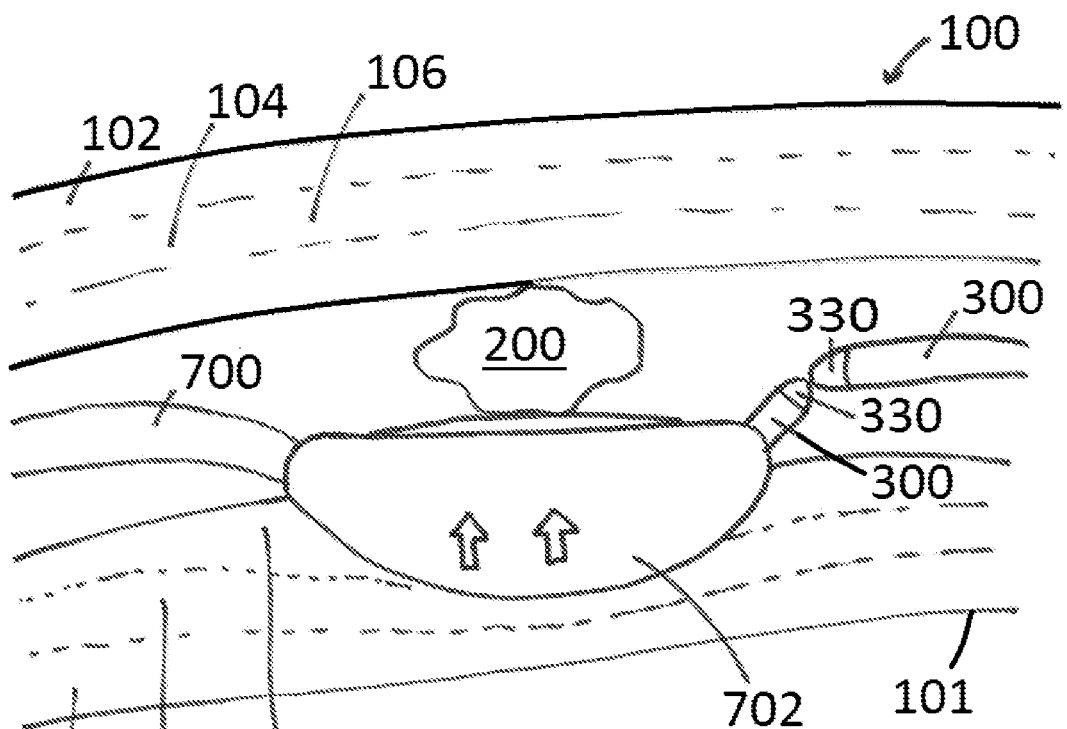
FIG. 8 shows a cut-away view of a vessel having an occlusion therein whereby a balloon of the balloon catheter is inflated to open the bypass lumen, according to at least one exemplary embodiment of the present disclosure An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

Once the procedure has been successfully performed, a balloon catheter 700, as shown in FIG. 7, can be advanced over device 300 so that a balloon 702 of balloon catheter 700 is positioned within the bypass lumen 202 adjacent to the occlusion 200. Inflation of the balloon, as shown in FIG. 8, can cause the bypass lumen 202 to expand so to be able to handle blood flow therethrough, which can, for example, move portion of vessel 100 in a direction identified by the arrows shown in FIG. 8 toward the occlusion. After a desired amount of time, balloon 702 can be deflated, and balloon catheter 700 can be removed along with devices 300, and the opening within the vessel 100 (the bypass lumen 202) would be formed therein, allowing blood to effectively flow past the occlusion 200 through the bypass lumen 202 (such as shown in FIG. 2), restoring active blood flow through that portion of the vessel 100 having the occlusion 200.

In some cases, and as noted above, one device 300 can be delivered in an antegrade direction through the vessel (such as artery 100). However, going through the antegrade direction is not always possible for various reasons, and instead device 300 can be delivered in a retrograde direction. Should only one direction be available, one device 300 could be used as described above, to be advanced into the lumen 110 of the vessel 100 to or near occlusion 200, into the tunica intima 106 to a location between the tunica intima 106 and the tunica media 104, advanced within the location between the tunica intima 106 and the tunica media 104 and back through the tunica intima 106 on the other side of occlusion 200 and into lumen 110 so to generate the bypass lumen 202 as referenced herein.

At the end of a successful procedure, the two ends of the wires are cut so to connect the same. Knowing the proximity of the two wires (distance between relative ends of said wires) and when they touch one another is valuable information to have with such a procedure.

In view of the same, the present disclosure includes disclosure of using two electrical sensing wires that can touch. When said wires (exemplary devices 300 of the present disclosure) would contact one another within a vessel, a conductance value (G) obtained by each wire would spike, providing said valuable information to the interventionalist. One the two devices 300 contact one another, as referenced herein, the interventionalist will know the location of the occlusion 200 and know that advancement of a balloon catheter 700, such as referenced herein, so that the balloon 702 of the balloon catheter 700 is within the vessel 100 itself so to be inflated to further open and create an effective bypass lumen 202.

While various embodiments of devices and systems for creating a bypass lumen in connection with a chronic total occlusion procedure and methods for performing the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:
1. A method, comprising the steps of:
introducing at least part of a first elongated body into a lumen of an artery so that a distal tip of the first elongated body is positioned on a first side of an occlusion within the lumen of the artery, wherein the distal tip of the first elongated body comprises an impedance detector, the impedance detector configured to measure first impedance data of the lumen and second impedance data of a wall of the artery, wherein the first impedance data is different from the second impedance data;

inserting the distal tip of the first elongated body into the wall of the artery in between a tunica media and a tunica intima of the artery;

identifying a change in impedance between contacting the tunica intima and contacting the tunica media;

advancing the distal tip of the first elongated body in between the tunica media and the tunica intima; and further advancing the distal tip of the first elongated body back into the lumen of the artery to generate a bypass lumen and so that the distal tip is positioned on an opposite second side of the occlusion within the lumen of the artery, wherein the distal tip of the first elongated body remains between the tunica media and the tunica intima until the distal tip of the first elongated body is advanced back into the lumen of the artery so that the distal tip is positioned on the opposite second side of the occlusion within the lumen of the artery.

2. The method of claim 1, further comprising the steps of:

advancing a balloon catheter over at least part of the first elongated body so that a balloon of the balloon catheter is positioned within the bypass lumen between the tunica media and the tunica intima of the artery adjacent to the occlusion; and inflating the balloon within the bypass lumen so to expand the bypass lumen.

3. The method of claim 2, further comprising the steps of:

deflating the balloon; and removing the balloon catheter and the at least part of the first elongated body from the artery to allow blood present within the lumen of the artery to flow through the bypass lumen.

4. The method of claim 3, performed to and sufficient to treat a chronic total occlusion (CTO) condition.

5. The method of claim 1, further comprising the step of:

introducing at least part of a second elongated body into the lumen of the artery so that a distal tip of the second elongated body is positioned on the opposite second side of the occlusion within the lumen of the artery;

wherein the step of further advancing is performed to further advance the distal tip of the first elongated body so that it contacts the distal tip of the second elongated body.

6. The method of claim 5, wherein the distal tip of the first elongated body is magnetically attracted to the distal tip of the second elongated body.

7. A method, comprising the steps of:

introducing at least part of a first elongated body into a lumen of an artery so that a distal tip of the first elongated body is positioned on a first side of an occlusion within the lumen of the artery, wherein the distal tip of the first elongated body comprises an impedance detector, the impedance detector configured to measure first impedance data of the lumen and second impedance data of a wall of the artery, wherein the first impedance data is different from the second impedance data;

inserting the distal tip of the first elongated body into the wall of the artery in between a tunica media and a tunica intima of the artery;

identifying a change in impedance between contacting the tunica intima and contacting the tunica media;

advancing the distal tip of the first elongated body in between the tunica media and the tunica intima;

further advancing the distal tip of the first elongated body back into the lumen of the artery to generate a bypass lumen and so that the distal tip is positioned on an opposite second side of the occlusion within the lumen of the artery, wherein the distal tip of the first elongated body remains between the tunica media and the tunica intima until the distal tip of the first elongated body is advanced back into the lumen of the artery so that the distal tip is positioned on the opposite second side of the occlusion within the lumen of the artery;

advancing a balloon catheter over at least part of the first elongated body so that a balloon of the balloon catheter is positioned within the bypass lumen between the tunica media and the tunica intima of the artery adjacent to the occlusion;

inflating the balloon within the bypass lumen so to expand the bypass lumen;

deflating the balloon; and removing the balloon catheter from the artery to allow blood present within the lumen of the artery to flow through the bypass lumen.

8. The method of claim 7, further comprising the step of:

introducing at least part of a second elongated body into the lumen of the artery so that a distal tip of the second elongated body is positioned on the opposite second side of the occlusion within the lumen of the artery;

wherein the step of further advancing is performed to further advance the distal tip of the first elongated body so that it contacts the distal tip of the second elongated body.

9. The method of claim 8, wherein the distal tip of the first elongated body is magnetically attracted to the distal tip of the second elongated body.

10. The method of claim 7, performed to and sufficient to treat a chronic total occlusion (CTO) condition.

* * * * *